United States Patent

Scampini

[11] Patent Number: 5,989,191
[45] Date of Patent: Nov. 23, 1999

[54] USING DOPPLER TECHNIQUES TO MEASURE NON-UNIFORM ROTATION OF AN ULTRASOUND TRANSDUCER

[75] Inventor: John F. Scampini, Lexington, Mass.

[73] Assignee: Hewlettt-Packard Company, Palo Alto, Calif.

[21] Appl. No.: 09/100,504

[22] Filed: Jun. 19, 1998

[51] Int. Cl.⁶ .................................................. A61B 8/06
[52] U.S. Cl. .......................... 600/453; 600/454; 600/459
[58] Field of Search .................................. 600/453, 454, 600/459, 462, 463, 465, 466, 467, 445, 446, 456; 73/658, 653; 342/25

[56] References Cited

U.S. PATENT DOCUMENTS

| | | | |
|---|---|---|---|
| 4,794,931 | 1/1989 | Yock | 128/660.03 |
| 4,917,097 | 4/1990 | Proudian et al. | 128/662.06 |
| 5,000,185 | 3/1991 | Yock | 128/662.03 |
| 5,159,931 | 11/1992 | Pini | 128/660.07 |
| 5,176,141 | 1/1993 | Bom et al. | 128/662.06 |
| 5,181,514 | 1/1993 | Solomon et al. | 128/660.09 |
| 5,186,177 | 2/1993 | O'Donnell et al. | 128/662.06 |
| 5,195,519 | 3/1993 | Angelsen | 600/446 |
| 5,240,003 | 8/1993 | Lancee et al. | 128/662.06 |
| 5,271,402 | 12/1993 | Yeung et al. | 128/660.1 |
| 5,284,148 | 2/1994 | Dias et al. | 128/662.06 |
| 5,465,624 | 11/1995 | Tseytlin et al. | 73/653 |
| 5,485,845 | 1/1996 | Verdonk et al. | 128/662.06 |
| 5,507,294 | 4/1996 | Lum et al. | 128/662.06 |
| 5,509,418 | 4/1996 | Lum et al. | 128/662.06 |
| 5,682,896 | 11/1997 | Scheib et al. | 600/456 |
| 5,699,806 | 12/1997 | Webb et al. | 128/660.09 |

FOREIGN PATENT DOCUMENTS

WO 90/14601  11/1990  WIPO ................ G01S 7/52

OTHER PUBLICATIONS

Brooks, Dana H., et al., "Electrical Imaging of the Heart," Signal Processing Magazine, pp. 24–42, (Jan. 1997).

Ollinger, John M., et al., "Positioning–Emission Tomography," Signal Processing Magazine, pp. 43–55, (Jan. 1997).

Wright, G.A., "Magnetic Resonance Imaging," Signal Processing Magazine, pp. 56–66, (Jan. 1997).

Quistgaard, Jens U., "Signal Acquistion and Processing in Medical Diagnostic Ultrasound," Signal Processing Magazine, pp. 67–74, (Jan. 1997).

Saini, Vasant D., PhD., et al., Chapter 1, "Basic Principles of Ultrasound and Doppler Effect," Doppler Echochariography, Fundamentals and Equipment, pp. 1–11, (1994).

Saini, Vasant D., PhD., Chapter 2, "Doppler Signal Analyses", Doppler Echocardiography, Fundamentals and Equipment, pp. 12–30 (1944).

(List continued on next page.)

*Primary Examiner*—Marvin M. Lateef
*Assistant Examiner*—Ali M. Imam

[57] ABSTRACT

According to one embodiment, an apparatus for measuring rotational velocity includes a support member, a transducer, and a Doppler shift measurement module. The transducer, which is supported by the support member, emits a first wave and detects a corresponding second wave reflected by matter intercepted thereby as the support member rotates continuously about an axis of rotation. The Doppler shift measurement module measures frequency shifting between the first wave and the second wave as the support member rotates about the axis of rotation, the frequency shifting being indicative of a rotational velocity of the support member relative to the matter. According to another embodiment, a method for analyzing motion of a transducer, includes the steps of: (a) emitting a wave from the transducer while a support member supporting the transducer is rotating; (b) detecting a portion of the wave that is reflected from matter intercepted thereby; and (c) measuring frequency shifting between a frequency of the wave and a frequency spectrum of the reflected portion of the wave.

20 Claims, 4 Drawing Sheets

OTHER PUBLICATIONS

Saini, Vasant D., PhD., et al., Chapter 3, "Principles of Doppler Ultrasound Implementation," Doppler Echocardiography, Fundamentals and Equipment, pp. 31–41 (1944).

Goldberg, Stanley J., MD, et al., Preface and Chapter 1, "History of Doppler Echocardiography", Doppler Echocardiography, pp. vii–7, (1988).

Goldberg, Stanley J., MD, et al., Chapter 2, "Doppler Physics for Physicians and Technologists," Doppler Echocardiography, pp. 9–36, (1988).

Missri, Jose, MD, Chapter 2, "Physical Principles and Instrumentation in Spectral and Color Doppler Flow Imaging," Clinical Doppler Echocardiography, Spectral and Color Flow Imaging, pp. 8–19, (Undated).

USING DOPPLER TECHNIQUES TO MEASURE NON-UNIFORM ROTATION OF AN ULTRASOUND TRANSDUCER

BACKGROUND OF THE INVENTION

1. Field of the Invention

The present invention relates to the generation of an Intravascular Ultrasound (IVUS) image from a mechanically rotating intravascular transducer and, more particularly, to measuring non-uniformity in the angular velocity of a rotating ultrasonic transducer.

2. Discussion of Related Art

Ultrasonic imaging is widely used in medicine. In particular, it can be used for making images from inside body cavities such as the vascular system, and thus aiding in the diagnosis of disease. A probe containing an ultrasonic transducer is inserted into the body area to be imaged. The transducer transmits an acoustic pulse into the body tissues, and detects the reflections of the pulse at tissue boundaries due to differences in acoustic impedance, as well as the back scattered sound from acoustically heterogeneous tissue. The differing times taken for the transducer to receive the reflected or back scattered ultrasound pulses correspond to differing distances of the tissues from the transducer. By stepping or sweeping the transducer through a set of selected angles, a two-dimensional ultrasound image corresponding to a map of the acoustic impedance boundaries or back scattering coefficients may be obtained. From this image, the condition of the body tissues can be determined. For example, the method of Intravascular Ultrasound (IVUS) sequentially transmits ultrasound pulses in equally spaced angular increments around all or part of a circle to obtain cross-sectional images of coronary arteries, thereby demonstrating areas of atherosclerotic plaque, calcification, etc.

Generally, there are two types of ultrasonic probes for IVUS imaging. The first type employs a synthetic aperture technique. For example, U.S. Pat. No. 4,917,097 (Proudian et al.) and U.S. Pat. No. 5,186,177 (O'Donnell et al.) teach how an ultrasonic pulse may be transmitted in a particular direction from a transducer using the method of synthetic aperture. Generally, this involves the sequential excitation of selected elements in an array of transducer elements.

The second type of IVUS probe scans tissue, for example, the tissue of the coronary artery, by the mechanical rotation of a mechanism that emits ultrasonic pulses and detects portions of the emitted pulses that are reflected from the tissue. The mechanically rotated type of probes include a few subclasses. In a first subclass, either a distal (remote from the operator) transducer or a distal mirror is rotated by an extended drive shaft driven by a proximal motor (e.g., U.S. Pat. No. 4,794,931 (Yock) and U.S. Pat. No. 5,000,185 (Yock)).

In a second subclass, the rotation is confined to the distal end, where either a miniature motor (e.g., U.S. Pat. No. 5,240,003 (Lancee et al.) and U.S. Pat. No. 5,176,141 (Bom et al.)) or a fluid driven turbine (e.g., U.S. Pat. No. 5,271,402 (Yeung et al.)) is used to rotate the transducer or mirror.

In a third subclass, a stationary proximal transducer is acoustically coupled to a rotating acoustic waveguide that guides the sound to and from the distal end (e.g., U.S. Pat. No. 5,284,148 (Dias et al.)).

In a fourth subclass, a turbine is rotated by an acoustic signal generated outside the vessel to direct another ultrasonic signal in a rotating fashion (e.g., U.S. Pat. No. 5,509,418 (Lum et al.)).

In a final subclass, an external driving member rotates a tube to rotate a reflecting element at the distal end of the tube to reflect ultrasound (e.g., U.S. Pat. No. 5,507,294 (Lum et al.)).

Presently, probes that direct ultrasonic pulses by mechanical rotation are more widely used than probes that electronically aim the pulses. The mechanical approach can be implemented using a single transducer, while the electronic approach requires an entire array of transducers to be contained in the distal end, which may be difficult to pass into the blood vessel of interest.

One concern in using an IVUS probe with mechanical rotation, however, is that the angular velocity of the rotating structure, e.g., the transducer, that directs the ultrasonic pulses may be non-uniform throughout the structures 360° range of rotation. If the rotating structure changes its angular velocity during each period of rotation (as is usually the case), then adjacent ultrasound pulses will be transmitted at non-uniform angular separations as the structure rotates. Such a system therefore will image tissues at uneven spatial intervals and the image produced by it will appear distorted.

One cause of this non-uniform angular velocity (in a catheter using a drive shaft) is mechanical friction between the spinning drive shaft and the surrounding stationary sheath as they bend through the tortuous path of the blood vessel. Although the proximal (near the operator) end of the drive shaft may be rotating at the desired angular velocity, any bending of the catheter along its length will cause the angular velocity of the distal end of the drive shaft to vary from the desired velocity as the distal end of the drive shaft moves to different positions within its 360-degree range of rotation.

One system that is capable of measuring and correcting the non-uniform angular velocity of IVUS transducers is described in U.S. Pat. No. 5,699,806 (Webb et al.), which is assigned to the assignee of the present application, and which is incorporated herein by reference.

U.S. Pat. No. 5,485,845 (Verdonk et al.) describes a technique for detecting nonuniformity in the angular velocity of an IVUS transducer by using an array of beacons positioned on a sheath in which the transducer is disposed. This method, however, requires special catheters that have delicate structural features added to them to make them function properly.

What is needed, therefore, is an improved technique for measuring the angular velocity of a rotating transducer.

SUMMARY OF THE INVENTION

According to one aspect of the present invention, an apparatus for measuring rotational velocity includes a support member, a transducer, and a Doppler shift measurement module. The transducer, which is supported by the support member, emits a first wave and detects a corresponding second wave reflected by matter intercepted thereby as the support member rotates continuously about an axis of rotation. The Doppler shift measurement module measures frequency shifting between the first wave and the second wave as the support member rotates about the axis of rotation, the frequency shifting being indicative of a rotational velocity of the support member relative to the matter.

According to another aspect, the first and second waves may include acoustic pulses.

According to yet another aspect, the matter may include a catheter surrounding the transducer, the transducer being rotatable within the catheter.

According to another aspect of the present invention, a method for analyzing motion of a transducer, includes the steps of: (a) emitting a wave from the transducer while a support member supporting the transducer is rotating; (b) detecting a portion of the wave that is reflected from matter intercepted thereby; and (c) measuring frequency shifting between a frequency of the wave and a frequency spectrum of the reflected portion of the wave.

BRIEF DESCRIPTION OF THE DRAWINGS

The following figures are included to better illustrate the embodiments of the present invention. In these figures, like numerals represent like features in the several views.

DETAILED DESCRIPTION OF THE INVENTION

Figure 1:
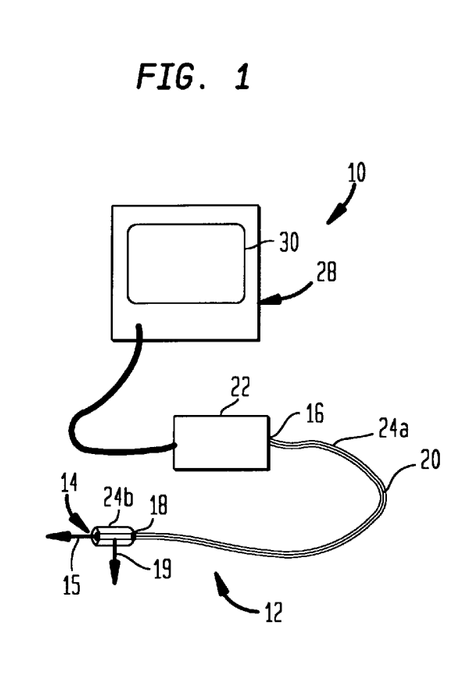
FIG. 1 is a perspective view of an ultrasound imaging apparatus that may be employed according to one embodiment of the present invention.

FIG. 1 shows an ultrasound apparatus 10 according to one embodiment of the present invention. Ultrasound apparatus 10 may be used, for example, to generate images of the inside portions of cavities, such as blood vessels or the heart, of the body of a patient. As shown, ultrasound apparatus 10 may include a flexible elongated probe 12, an ultrasonic transducer 18, a catheter 24 (including a sleeve-portion 24a and a tip-portion 24b), an external motor 22, a controller 28, and a display apparatus 30. Elongated probe 12 may include a shaft 20 surrounded by sleeve-portion 24a so that shaft 20 is rotatable within sleeve-portion 24a.

Transducer 18 may be any suitable ultrasonic transducer that is capable of emitting ultrasonic pulses during first time periods and detecting reflected portions of the emitted pulses during second time periods. Transducer 18 may include two or more separate transducer elements, e.g., one transducer element to emit ultrasonic pulses and another transducer element to detect reflected pulses, or may constitute a single transducer element that both emits and detects ultrasonic pulses (during different time periods).

Ultrasonic transducer 18 may be mounted on flexible shaft 20 at a distal end 14 of probe 12 so that ultrasonic pulses are emitted and received by transducer 18 in a direction 19 that is substantially perpendicular to a direction 15 in which distal end 14 is oriented. Tip-portion 24b of catheter 24 may surround transducer 18 such that transducer 18 may rotate within tip-portion 24b. A guide wire (not shown) may be used to guide tip-portion 24b of catheter 24 and transducer 18 to an appropriate location within the body of a patient, e.g., within a blood vessel.

Motor 22 may be connected to shaft 20 adjacent a proximate end 16 of probe 12 so that motor 22 may rotate shaft 20 within sleeve-portion 24a. Sleeve-portion 24a preferably remains stationary with respect to both tip-portion 24b and motor 22, while shaft 20 rotates within sleeve-portion 24a and transducer 18 rotates within tip-portion 24b, thereby minimizing the risk of tissue damage caused by moving components. As motor 22 causes shaft 20 to rotate within sleeve-portion 24a of catheter 24, transducer 18 will rotate at a particular angular velocity within tip-portion 24b and a series of ultrasonic pulses will be emitted and detected by transducer 18 as it rotates.

Ideally, transducer 18 will be rotated at a uniform angular velocity throughout its 360-degree range of rotation so that the angular separation between sequential pulses is substantially constant. Often, however, transducer 18 will rotate at a non-uniform angular velocity, even if motor 22 is rotating at a constant angular velocity; because drive shaft 20 will twist as it rotates since the degree of twisting in drive shaft 20 of an IVUS imager is limited (much like a torsion bar), the average angular velocity of distal end 14 of drive shaft 20 remains the same as the average angular velocity of proximal end 16, even though distal end 14 sometimes rotates more quickly, and sometimes rotates more slowly, than proximal end 16.

The non-uniformity in the angular velocity of distal end 14 of drive shaft 20 is substantially the same during each revolution of drive shaft 20. Thus, the ultrasonic energy that is reflected or scattered from a particular portion of tissue may be portrayed in the resulting two-dimensional image of the tissue as being at a location that is offset from its actual location.

Once the non-uniformity in the angular velocity of transducer 18 is measured, controller 28 may be used to correct or compensate for it using known techniques. For example, controller 28 may: (1) adjust the rotational speed of shaft 20 at particular time intervals during each 360-degree rotation thereof, (2) adjust an image construction algorithm to reconstruct the image to appear as it would have appeared if the pulses had been separated uniformly, (3) adjust the pulse rate throughout the transducer's 360 degree range of rotation to account of its rotational non-uniformity, or (4) increase the pulse rate to over-sample the image and select only those samples that were taken at substantially uniform angular intervals. Examples of at least some of these correction techniques, are described in U.S. Pat. No. 5,485,845 to Verdonk et al., which is incorporated herein by reference.

Figure 2:
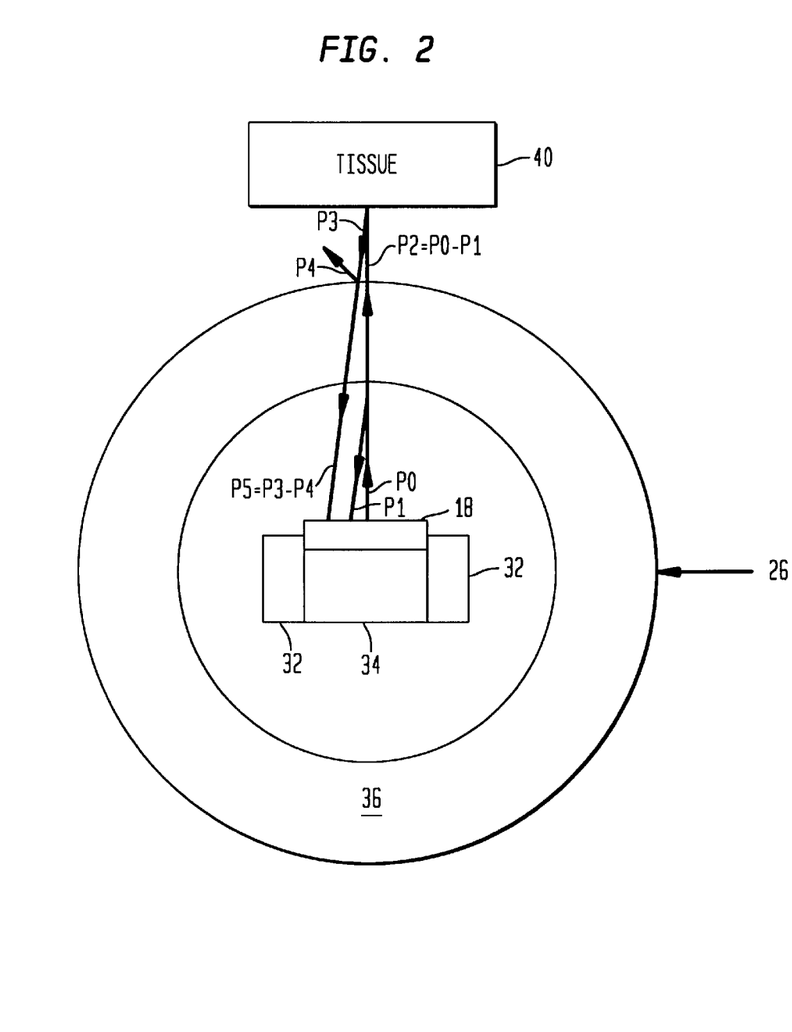
FIG. 2 is a cross-sectional view of an embodiment of the transducer and catheter shown in FIG. 1.

FIG. 2 shows a cross-section of transducer 18 and tip-portion 24b of catheter 24 (shown in FIG. 1), and illustrates how an ultrasonic pulse (P0) emitted from transducer 18 may be reflected or scattered by tip-portion 24b and a tissue mass 40. As shown, transducer 18 may be mounted on a holder 32 and may be backed by a backing 34, which absorbs acoustic energy from the back of transducer 18. Transducer 18, backing 34 and holder 32 may be mounted to the distal end 14 of drive shaft 20 (shown in FIG. 1). Thus, as drive shaft 20 rotates, transducer 18, backing 34 and holder 32 can rotate as a unit within tip-portion 24b. Transducer 18, holder 32 and backing 34 all may be immersed in a saline solution contained within tip-portion 24b, which solution aids in the propagation of acoustic waves.

Tip-portion 24b of catheter 24 preferably is made of a material 36 having a predetermined acoustic reflectivity so that a small portion (P1) of each pulse (P0) emitted by transducer 18 will be reflected by tip-portion 24b back to transducer 18. The remaining portion (P2) of each emitted pulse passes through tip-portion 24b to the surrounding bodily tissue 40. When this remaining portion (P2) of the pulse intercepts surrounding tissue 40, a portion (P3) of it is reflected or scattered back toward rotating transducer 18. A small portion (P4) of this reflected or scattered portion (P3) is deflected by tip-portion 24b, and the remaining portion (P5) of this reflected or scattered portion (P3) reaches transducer 18 and is detected thereby. It is this portion (P5) of each emitted pulse (P0) that, after being detected by transducer 18, is used to construct an image of the surrounding tissue. Pulse portions P0–P5 are shown as being oriented in different angular directions for purposes of illustration only. In actuality, all would be oriented in substantially the same angular direction.

According to one embodiment of the invention, the portion (P1) of each pulse (P0) that is reflected from tip-portion 24b of catheter 24 back to transducer 18 may be analyzed by a Doppler shift measurement module 156 (shown in FIG. 7) within controller 28 using Doppler techniques (described below) to determine the relative rotational velocity of transducer 18 throughout each 360-degree rotation thereof. Since typical imaging frequencies are in the range of 10 to 30 MHZ, many currently-existing catheters already are made of materials that reflect sufficient amounts of the emitted acoustic pulses to make measurements of Doppler shifts (explained below) between the emitted and reflected pulses possible. Therefore, in many situations, a specifically-doped catheter will not be required.

According to one embodiment, a Pulsed Wave Doppler (PWD) technique may be used to measure the relative rotational velocity of transducer 18 within tip-portion 24b. While transducer 18 is rotating, it may transmit pulses of ultrasonic waves (e.g., P0) at a first frequency $f_0$ towards the surrounding tissue. For each ultrasonic pulse (P0) emitted by transducer 18, the reflected portion (P1) of the emitted pulse (P0) will be reflected by tip-portion 24b and will reach transducer 18 after only a brief time period. Because pulse (P1) will be reflected from tip-portion 24b while transducer 18 is rotating within tip-portion 24b, the frequency spectrum of pulse (P1) will spread in both the positive and negative directions by an amount dependent on the rotational velocity of transducer 18 within tip-portion 24b, as explained below. The amount of frequency shifting (i.e., the Doppler spectrum) between each emitted pulse P0 and the corresponding reflected portion (P1) therefore may be measured to determine the relative velocity of transducer 18 as it rotates.

Portion (P5) of each emitted pulse (P0) will reach transducer 18 (after being reflected by tissue 40) a particular time period after transducer 18 has detected the corresponding reflected pulse portion (P1) of pulse (P0). Because tissue 40 is not necessarily a constant distance from transducer 18, however, the frequency spectrum of portion P5 (which is reflected from tissue 40) will not necessarily shift in direct proportion to changes in rotational velocity of transducer 18. Thus, it is preferable to measure only the frequency spectrum of reflected portion (P1), and not reflected portion (P5), when performing a Doppler spectrum analysis to analyze the rotational velocity of transducer 18 within tip-portion 24b.

Thus, by measuring the frequency of pulses detected by transducer 18 during only a brief time window between: (a) a time that each reflected portion P1 of an emitted pulse (P0) first reaches transducer 18, and (b) a time that the corresponding reflected portion P5 of the emitted pulse (P0) first reaches transducer 18, only the ultrasonic pulses reflected by tip-portion 24b will be detected and analyzed for frequency shifting.

Figure 3:
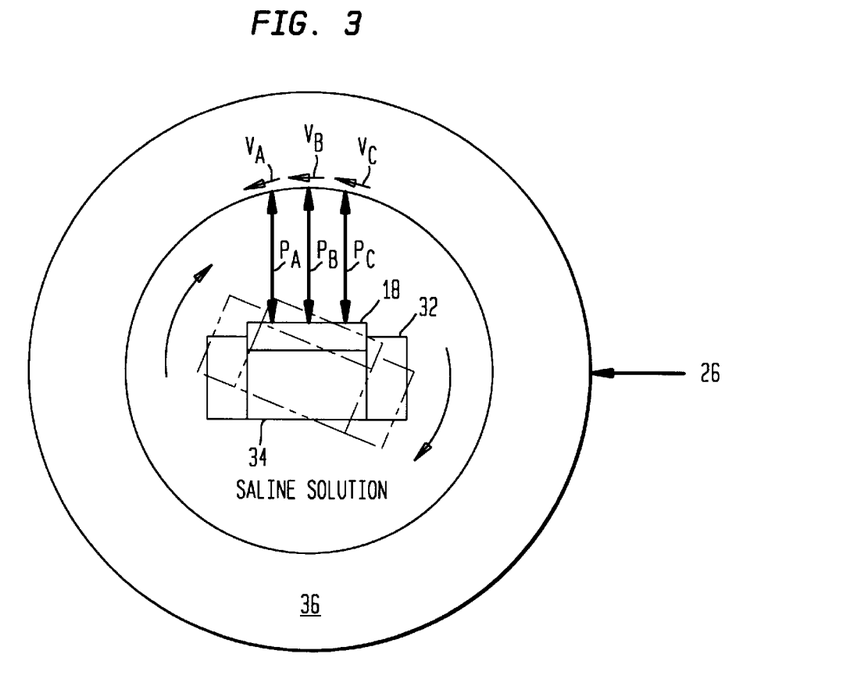
FIG. 3 is a cross-sectional view of the transducer and catheter shown in FIG. 2 showing the transducer rotating within the catheter.
Figure 4A:
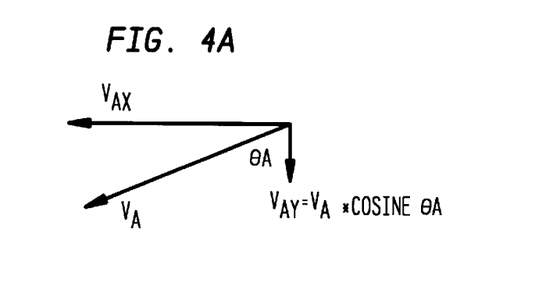
FIGS. 4a–4c are graphs illustrating the components of velocity vectors Va, Vb and Vc shown in FIG. 3.
Figure 4B:
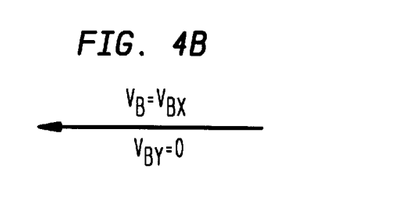
Figure 4C:
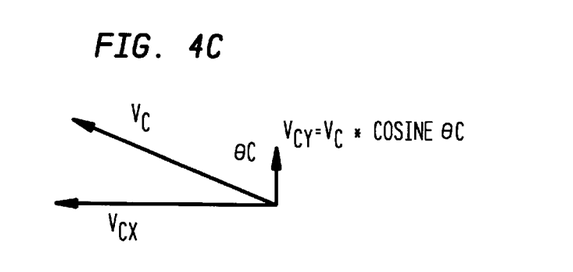

FIGS. 3 and 4 illustrate how the rotation of transducer 18 within tip-portion 24b of catheter 24 can affect the frequency of ultrasonic pulses reflected from tip-portion 24b. As shown in phantom lines in FIG. 3, transducer 18, holder 32 and backing 34 may rotate clockwise within tip-portion 24b. For ease of understanding, however, it is useful to envision transducer 18 as remaining stationary and tip-portion 24b as rotating counterclockwise about transducer 18. Additionally, although transducer 18 generally emits only one ultrasonic pulse (oscillating at a particular frequency) at a time, for the purposes of illustration, it is useful to assume that transducer 18 concurrently transmits three separate (relatively narrow) ultrasonic pulses $P_A$, $P_B$, and $P_C$ each oscillating at a frequency $f_0$, from different portions of transducer 18.

Still assuming that transducer 18 remains stationary as tip-portion 24b rotates about it, velocity vectors $V_A$, $V_B$ and $V_C$ in FIG. 3 illustrate the direction in which tip-portion 24b is moving relative to transducer 18 at the points where pulses $P_A$, $P_B$ and $P_C$, respectively, intercept an inner surface of tip-portion 24b. The magnitudes of these vectors always will be equal to one another. But, as illustrated in FIG. 4, the components of vectors $V_A$, $V_B$ and $V_C$ that are oriented in the direction toward or away from transducer 18, i.e., components $V_{AY}$, $V_{BY}$ and $V_{CY}$, respectively, are different for the different points on the inner surface of tip-portion 24b. That is, pulse $P_A$ intercepts a point on the inner surface of tip-portion 24b that is moving towards transducer 18 at a rate of $V_{AY}$, pulse $P_B$ intercepts a point on the inner surface of tip-portion 24b that is stationary with respect to transducer 18, and pulse $P_C$ intercepts a point on the inner surface of tip-portion 24b that is moving away from transducer 18 at a rate of $V_{CY}$.

Because each of pulses $P_A$ and $P_C$ intercepts a portion of tip-portion 24b that is in motion relative to transducer 18, the oscillation frequencies of the reflected portions of these pulses will be shifted by amounts dependent on the rotational velocity of transducer 18 within tip-portion 24b. Specifically, the oscillation frequency of pulse $P_A$ will be increased by an amount dependent on the rotational velocity of transducer 18 and the oscillation frequency of pulse $P_C$ will be decreased by an amount dependent on the rotational velocity of transducer 18. Thus, if each of pulses $P_A$, $P_B$ and $P_C$ oscillates at a frequency of $f_0$ when it is emitted from transducer 18, then, when each of them is reflected by tip-portion 24b and detected by transducer 18, pulse $P_A$ will have a frequency $f_A$ (wherein $f_A > f_0$), pulse $P_B$ will have a frequency $f_0$, and pulse $P_C$ will have a frequency $f_C$ (wherein $f_C < f_0$).

For each of the three transmitted pulses $P_A$, $P_B$ and $P_C$ the difference between the reflected frequencies $f_A$, $f_B$ and $f_C$ and the transmitted frequency $f_0$ (i.e., $f_A-f_0$, $f_B-f_0$, and $f_C-f_0$) is the respective Doppler shift ($\pm\Delta f$) in the frequency of the pulse. Once this frequency shift is measured, each of velocity vectors $V_{AY}$, $V_{BY}$ and $V_{CY}$ may be determined using the Doppler effect formula, i.e., $V=c(\pm\Delta f)/(2 f_0)$, wherein the Doppler shift ($\pm\Delta f$) is the difference between the emitted frequency ($f_0$) and the detected frequency (e.g., $f_A$, $f_B$ or $f_C$), and c is the propagation velocity of sound.

As discussed above, however, an ultrasonic transducer typically emits only one pulse at a time. Therefore, the three distinct pulses $P_A$, $P_B$ and $P_C$ described above, in reality, constitute a single (relatively wide) pulse that intercepts an entire section of the inner surface of tip-portion 24b. The reflection of this single pulse from a section of transducer 18 therefore will cause a gradual spread in the frequency spectrum of the reflected pulse, rather than the distinct frequency shifts illustrated in FIG. 3.

Doppler shift measurement module 156 (shown in FIG. 7) may compare the oscillation frequencies of the pulses emitted from transducer 18 (which all are the same frequency) to the frequency spectrums of the corresponding pulses reflected from tip-portion 24b of catheter 24 and detected by transducer 18 during the brief time windows discussed above, and may output positive and negative mean velocity waveforms representing, respectively, the current mean positive and negative means velocities of tip-portion 24b relative to transducer 18.

Figure 7:
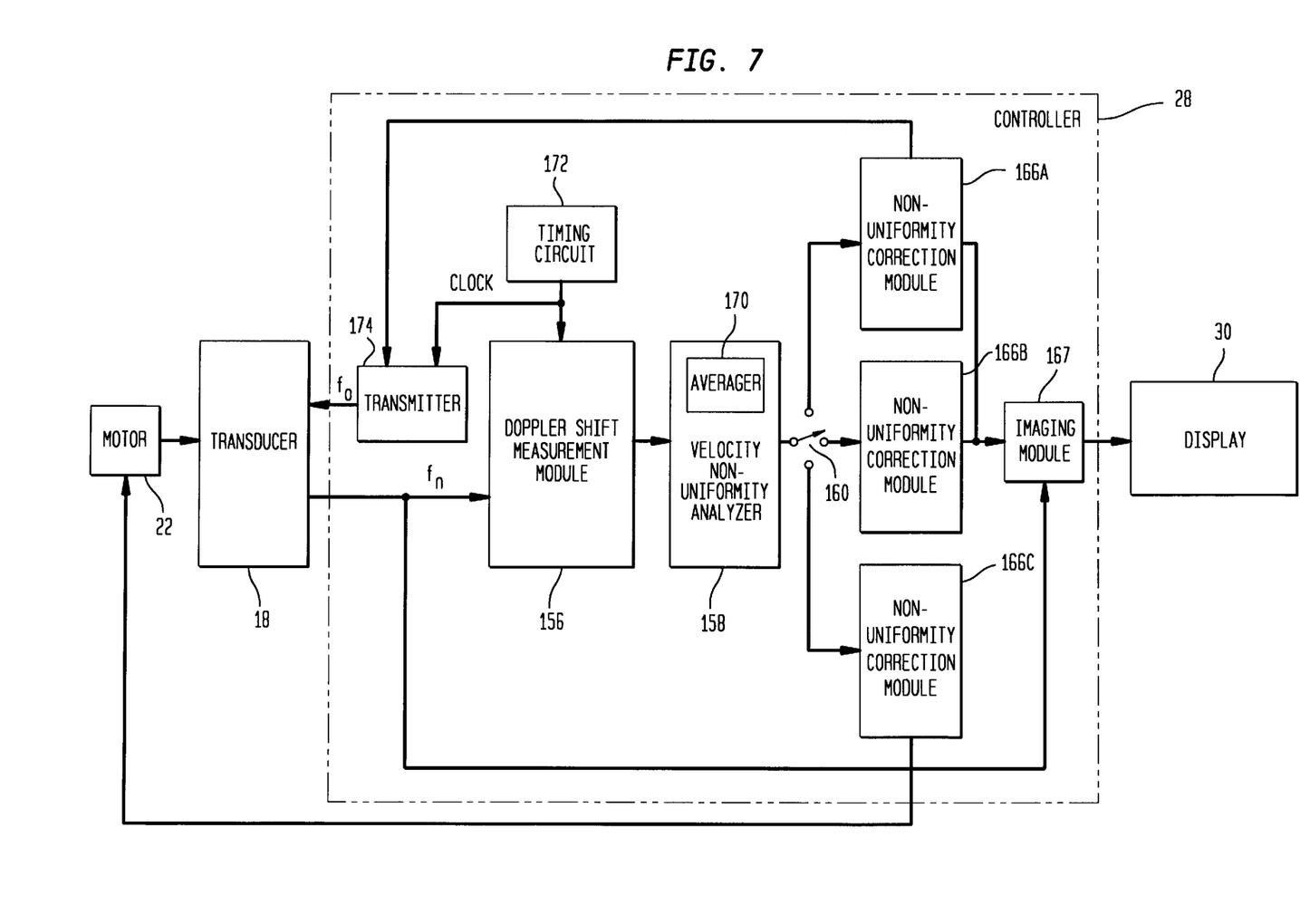
FIG. 7 is a block diagram showing one possible embodiment of the apparatus shown in FIG. 1.

The generation of these positive and negative mean velocity waveforms may be accomplished, for example, as follows. First, each of the signals used to cause transducer 18 to emit ultrasonic pulses (all of which oscillate at the same frequency) may be mixed with a corresponding signal generated by transducer 18 in response to the detection of the portion of the emitted signal that has been reflected from tip-portion 24b. This mixing may be performed during the brief time windows (described above) between: (1) times at which transducer 18 first detects pulses reflected from catheter 18, and (2) times at which transducer 18 first detects pulses reflected from tissue 40.

The signals produced by this mixing may then be converted into frequency domain amplitude spectrums, e.g., using a fast Fourier transform (FFT) technique. Because of the mixing, each frequency domain amplitude spectrum so produced will straddle the baseband frequency of zero hertz. Since each frequency domain amplitude spectrum is represented digitally in this embodiment, the spectrum will include a large number of discrete points (e.g., 128 discrete points) at any given moment, each of which having an amplitude coordinate and a frequency coordinate within the spectrum.

Next, for at least one moment during the time period that each frequency domain amplitude spectrum is produced, a so-called "weighted velocity value" may be calculated for each of the points in the spectrum by multiplying: (a) the result of the Doppler formula $V=c(\pm\Delta f)/(2 f_0)$, wherein ($\pm\Delta f$) represents the frequency coordinate of the point and ($f_0$) represents the oscillation frequency of the signal used to cause transducer 18 to emit ultrasonic pulses, by (b) the amplitude coordinate of the point. The averages may then be calculated of: (1) the weighted velocities corresponding to positive frequency coordinates, and (2) the weighted velocities corresponding to negative frequency coordinates. These averages represent discrete points of the positive and negative mean velocity waveforms, respectively. It should be understood that this is only one example of a method by which these waveforms may be generated and that other techniques may alternatively be used to accomplish a similar result or other signals containing similar information may alternatively be generated.

Figure 5:
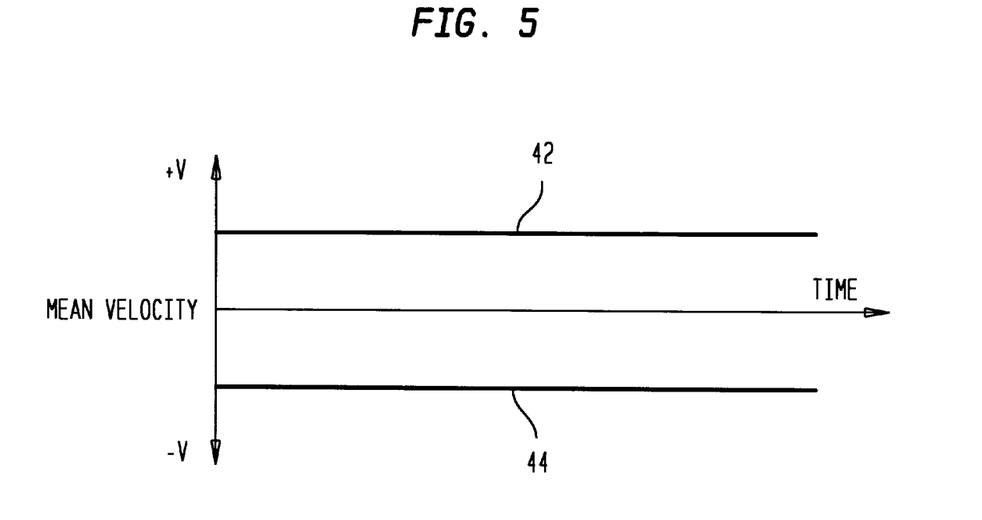
FIGS. 5 and 6 are graphs illustrating positive and negative mean velocity wave forms that may be output from a Doppler shift measurement module employed according to one embodiment of the invention.

FIG. 5 is a graph showing positive and negative mean velocity waveforms that may be output from Doppler shift measurement module 156 when transducer 18 is rotating at a uniform angular velocity within tip-portion 24b of catheter 24. As shown, curve 42 represents the positive mean velocity waveform and curve 44 represents the negative mean velocity waveform from Doppler shift measurement module 156 over one rotational cycle of transducer 18. Because transducer 18 is rotating at a constant velocity within tip-portion 24b, the positive and negative mean velocity waveforms are constant throughout the rotational cycle.

Figure 6:
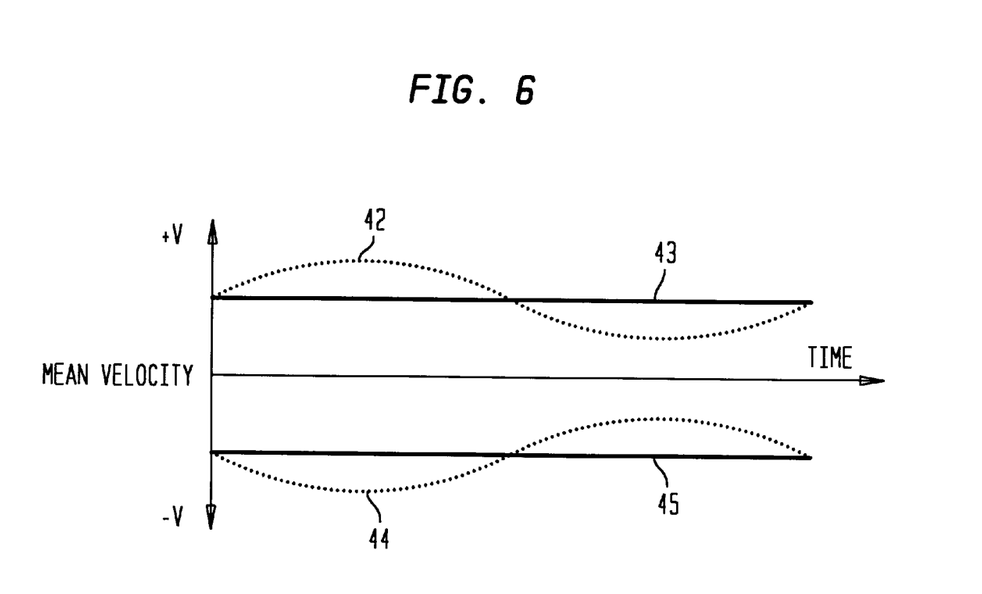

FIG. 6 is a graph showing positive and negative mean velocity waveforms that may be output from Doppler shift measurement module 156 when transducer 18 is rotating at a non-uniform angular velocity within tip-portion 24b of catheter 24. As in FIG. 5, curve 42 represents the positive mean velocity waveform and curve 44 represents the negative mean velocity waveform from Doppler shift measurement module 156 over one rotational cycle of transducer 18. As shown, the varying rotational velocity of transducer 18 can cause both the positive and negative mean velocity waveforms to fluctuate throughout the cycle. These changes in positive and negative mean velocity, as measured by the Doppler shift measurement module, correspond directly with changes in the rotational velocity of transducer 18 within tip-portion 24b.

Because transducer 18 may be driven by motor 22 (shown in FIG. 1) with a constant known velocity, the average actual angular velocity of transducer 18 over one full revolution will be equal to the known constant velocity of motor 22. Hence, for various points in the 360-degree cycle of transducer 18, the actual angular velocity of transducer 18 will be either equal to, or will be a particular percentage less than or greater than, the known constant velocity of motor 22.

According to one embodiment of the invention, an average amplitude of either: (1) the positive mean velocity waveform, (2) the negative mean velocity waveform, or (3) the sum of the absolute values of the positive and negative mean velocity waveforms, is measured over one full revolution of transducer 18. For example, curve 43 (FIG. 6) represents the per-cycle average amplitude of the positive mean velocity waveform (i.e., curve 42), and curve 45 represents the per-cycle average amplitude of the negative mean velocity waveform (i.e., curve 44).

Thus, when transducer 18 is oriented at any angular position within its 360-degree range of rotation, the current amplitudes of the waveforms from the Doppler shift measurement module 156 will be equal to, or will be a particular percentage greater than or less than, the per-cycle average amplitude of the waveforms. Because any changes in the angular velocity of transducer 18 correspond directly with changes in the amplitude of the waveform(s) from Doppler shift measurement module 156, the percentage difference between the known constant velocity of motor 22 (which is equal to the per-cycle average angular velocity of transducer 18) and the current actual angular velocity of transducer 18 will be approximately equal to the percentage difference between the per-cycle average amplitude of the waveform(s) and the current amplitude of the waveform(s).

Thus, the percentage difference between the known constant velocity of motor 22 driving transducer 18 and the current angular velocity of transducer 18, at any point throughout its 360 degrees of rotation, may be calculated based on one or more output waveforms from Doppler shift measurement module 156.

The mean velocity waveforms output from Doppler shift measurement module 156 may change from spectral sample to spectral sample due to noise or slight variations in the reflectivity of the catheter lens material. It is possible, however, to filter the mean velocity waveforms depending on the rotational speed of transducer 18 and/or the mechanical properties of the catheter that limit the possible velocity changes of transducer 18.

FIG. 7 is a block diagram showing an exemplary embodiment of the invention. As shown, controller 28 may include a timing circuit 172, a transmitter 174, a Doppler shift measurement module 156, a velocity non-uniformity analyzer 158, non-uniformity correction modules 166A–C, and an imaging module 167. Each of these modules may comprise separate hardware units, software routines, or any combination of hardware and software.

As shown, timing circuit 172 may provide a clock signal (oscillating at a frequency $f_0$) both to transmitter 174 and to Doppler shift measurement module 156. In response to this clock signal, transmitter 174 may transmit an electronic signal (oscillating at a frequency $f_0$) to transducer 18. Transducer 18, in turn, may use this electronic signal to generate ultrasonic pulses to be used for ultrasonic imaging, as described above. Doppler shift measurement module 156 may use the clock signal from timing circuit 172 to mix a signal from transducer 18 to baseband, as described above, to perform measurements regarding the rotational velocity of transducer 18.

As shown in the exemplary embodiment of FIG. 7, in addition to the clock signal from timing circuit 172, Doppler shift measurement module 156 may receive an electronic signal (having a frequency spectrum $f_n$) that is generated by transducer 18 when acoustic pulses that have been reflected by tip-portion 24b of catheter 24 are detected by transducer 18.

Based upon these signals, Doppler shift measurement module 156 may analyze the variance between the frequency $f_0$ of the clock signal (used to generate the emitted ultrasonic pulses) and the frequency spectrums $f_n$ of reflected ultrasonic pulses to generate positive and negative mean velocity waveforms, as described above. According to one embodiment, Doppler shift measurement module 156 generates a single waveform representing a sum of the absolute values of the positive and negative mean velocities, and outputs this waveform to velocity non-uniformity analyzer 158.

As shown, velocity non-uniformity analyzer 158 may include an averager 170. Averager 170 may calculate: (1) the average amplitude of the positive mean velocity waveform, (2) the average amplitude of the negative mean velocity waveform, or (3) the average amplitude of the sum of the absolute values of the positive and negative mean velocity waveforms, over each full 360-degree rotational cycle of transducer 18. Using this average amplitude, velocity non-uniformity analyzer 158 may calculate the variance between the per-cycle average amplitude and the current amplitude of the positive mean velocity waveform, the negative mean velocity waveform, or the absolute value of the sum of the two, to determine a percentage difference therebetween. As noted above, this percentage difference corresponds directly with the percentage difference between the current angular velocity of transducer 18 and the average angular velocity of transducer 18 over a complete rotational cycle (which should be equal to the known angular velocity of motor 22).

In the exemplary embodiment shown in FIG. 7, depending on the position of switch 160, any one of three velocity non-uniformity correction modules 166A–C may be selected to receive information from velocity non-uniformity analyzer 158 regarding any non-uniformity in the rotational velocity of transducer 18 measured thereby. In the embodiment shown: (1) correction module 166A may: (a) direct transmitter 174 to change the sampling rate of transducer 18 throughout its 360-degree range of rotation to account for its rotational non-uniformity, or (b) direct transmitter 174 to cause transducer 18 to over-sample the tissue and concurrently direct imaging module 167 to select only those samples having a substantially uniform angular separation between them, (2) correction module 166B may vary the algorithm used by imaging module 167 such that images may be reconstructed to appear as they would have appeared if the angular velocity of transducer 18 had been uniform, and (3) correction module 166C may vary the speed of motor 22 to change the rotational velocity of transducer 18 at appropriate times during each rotational cycle of transducer 18 such that transducer 18 rotates at a substantially uniform angular velocity. After being corrected or compensated for, the image generated by imaging module 167 may be displayed on display 30, which may constitute a monitor, printer, plotter, or the like.

It should be appreciated that the embodiment in FIG. 7 is only one example of a system that may be used to implement the invention, and that some of the modules shown can be combined, or subdivided into additional modules, either as electronic circuits, or as computer program functional blocks.

While one embodiment of the invention has been described herein as using ultrasonic waves to measure the non-uniformity in the angular velocity of a transducer, the waves used to measure this non-uniformity need not be ultrasonic and can be any other type of wave that is susceptible to a measurable Doppler shift. For example, electromagnetic waves could alternatively be employed.

Additionally, while one embodiment of the invention measures rotational velocity based upon a measured Doppler shift of waves reflected from a catheter in which a transducer is rotating, the surface from which the waves are reflected need not be a catheter and may alternatively be any other surface that is capable of reflecting waves.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. An apparatus for measuring rotational velocity, comprising:
    a support member which is rotatable about an axis of rotation;
    a transducer, coupled to the support member, to emit at least one first wave and to detect at least one corresponding second wave reflected by matter intercepted thereby as the support member rotates about the axis of rotation; and
    a Doppler shift measurement module coupled to the transducer, the Doppler shift measurement module measuring frequency shifting between the at least one first wave and the at least one second wave as the support member rotates about the axis of rotation, the frequency shifting being indicative of a rotational velocity of the support member relative to the matter.

2. The apparatus as claimed in claim 1, wherein the at least one first wave includes at least one first acoustic pulse and the at least one second wave includes at least one second acoustic pulse.

3. The apparatus as claimed in claim 1, wherein the at least one first wave includes a first plurality of acoustic pulses and the at least one second wave includes a second plurality of acoustic pulses.

4. The apparatus as claimed in claim 3, wherein the first and second pluralities of acoustic pulses are emitted and detected, respectively, during each rotational cycle of the transducer, and
    the apparatus further includes a non-uniformity correction module to select for imaging particular ones of the second plurality of acoustic pulses that have a substantially uniform angular separation therebetween.

5. The apparatus as claimed in claim 1, wherein the matter includes a catheter surrounding the transducer, the transducer being rotatable within the catheter.

6. The apparatus as claimed in claim 5, wherein the catheter is doped such that, for each at least one first wave emitted by the transducer, the catheter concurrently permits a first portion of the at least one first wave to pass through it and causes a second portion of the at least one first wave to be reflected back to the transducer, the second portion of the at least one first wave constituting the at least one second wave.

7. The apparatus as claimed in claim 6, wherein the Doppler shift measurement module measures frequency shifting between the at least one first wave and the second portion of the at least one first wave during a time period between when the transducer first detects the second portion of the at least one first wave and when the transducer first detects a portion of the first portion of the at least one first wave that has been reflected from matter external to the catheter.

8. The apparatus as claimed in claim 1, wherein the support member includes an elongated probe having a distal end, the transducer being mounted on the distal end of the probe.

9. The apparatus as claimed in claim 8, wherein the distal end of the probe is oriented in a first direction and the transducer is oriented to emit the at least one first wave in a second direction, which is transverse to the first direction.

10. The apparatus as claimed in claim 1, further comprising a motor mechanically coupled to the support member to rotate the support member.

11. The apparatus as claimed in claim 10, wherein a rotational speed of the motor can be varied in response to a signal from the Doppler shift measurement module to make the rotational velocity of the transducer substantially constant throughout each rotational cycle thereof, the signal being generated based upon the frequency shifting between the at least one first wave and the at least one second wave measured by the Doppler shift measurement module.

12. The apparatus as claimed in claim 1, wherein the Doppler shift measurement module is configured to output a signal indicative of one of a mean positive velocity, a mean negative velocity, and a sum of absolute values of the mean positive and negative velocities of the transducer relative to the matter.

13. The apparatus as claimed in claim 12, wherein the apparatus further comprises:

a velocity non-uniformity analyzer, coupled to the Doppler shift measurement module to receive the signal outputted therefrom, to calculate an average value of the one of the mean positive velocity, the mean negative velocity, and the sum of the absolute values of the mean positive and negative velocities over a complete revolution of the transducer, and to calculate, for a plurality of points in the revolution, a difference in velocity between the average value of the one of the mean positive velocity, the mean negative velocity, and the sum of the absolute values of the mean positive and negative velocities and a current value of the one of the mean positive velocity, the mean negative velocity, and the sum of the absolute values of the mean positive and negative velocities.

14. A method for measuring rotational velocity of a transducer, comprising steps of:

(a) emitting at least one wave from the transducer while a support member supporting the transducer is rotating;

(b) detecting a portion of the at least one wave that is reflected from matter intercepted thereby; and (c) measuring Doppler frequency shifting between a frequency of the at least one wave and a frequency spectrum of the reflected portion of the at least one wave.

15. The method as claimed in claim 14, wherein:

step (a) includes emitting at least one acoustic pulse from the transducer while the support member supporting the transducer is rotating;

step (b) includes detecting a portion of the at least one acoustic pulse that is reflected from matter intercepted thereby; and step (c) includes measuring frequency shifting between a frequency of the at least one acoustic pulse and a frequency spectrum of the reflected portion of the at least one acoustic pulse.

16. The method as claimed in claim 15, wherein step (b) includes detecting a portion of the at least one acoustic pulse that is reflected from a catheter in which the transducer is rotating.

17. The method as claimed in claim 14, wherein:

step (a) includes emitting a plurality of acoustic pulses from the transducer while the support member supporting the transducer is rotating; and step (b) includes detecting corresponding portions of the plurality of acoustic pulses that are reflected from matter intercepted thereby; and step (c) includes measuring frequency shifting between frequencies of the plurality of acoustic pulses and frequency spectrums of the corresponding reflected portions of the plurality of acoustic pulses.

18. The method as claimed in claim 17, wherein:

step (a) includes emitting the plurality of acoustic pulses from the transducer during one rotational cycle of the transducer;

step (b) includes detecting the corresponding portions of the plurality of acoustic pulses during the one rotational cycle of the transducer; and the method further includes the step of:

(d) in response to the frequency shifting measured in step (c), selecting for imaging ones of the corresponding reflected portions of the plurality of acoustic pulses that have a substantially uniform angular separation therebetween.

19. The method as claimed in claim 14, further including the step of:

(d) using the frequency shifting measured in step (c) to measure any non-uniformity in the angular velocity of the support member relative to the matter.

20. The method as claimed in claim 19, further including the step of:

(e) accounting for the non-uniformity in the angular velocity of the support member relative to the matter measured in step (d).

* * * * *